United States Patent [19]

Benelli et al.

[11] Patent Number: 4,988,691
[45] Date of Patent: Jan. 29, 1991

[54] ISOXAZOLE CONTAINING COMPOUNDS EXHIBITING ANTI-SEROTONIN ACTIVITY

[75] Inventors: Giancarlo Benelli, Milan; Angelo Carenzi, Busto Arsizio; Dario Chiarino, Monza; Mario Fantucci, Milan, all of Italy

[73] Assignee: Zambon Group S.p.A., Vicenza, Italy

[21] Appl. No.: 461,807

[22] Filed: Jan. 8, 1990

[30] Foreign Application Priority Data

Jan. 9, 1989 [IT] Italy ................. 19029 A/89

[51] Int. Cl.⁵ .................. A61K 31/46; C07D 451/12; C07D 451/04
[52] U.S. Cl. ................................... 514/214; 514/299; 514/304; 514/305; 514/326; 514/378; 540/582; 546/112; 546/125; 546/133; 546/137; 546/183; 546/209; 548/248
[58] Field of Search ............... 540/582; 546/112, 133, 546/137, 125, 183, 209; 548/248; 514/214, 299, 304, 305, 326, 378

[56] References Cited

U.S. PATENT DOCUMENTS 4,636,513   1/1987   Kämmerer et al. ............... 546/209

Primary Examiner—Bernard Dentz
Attorney, Agent, or Firm—Stevens, Davis, Miller & Mosher

[57] ABSTRACT

Compounds of formula

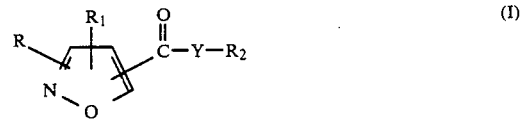

(wherein R, $R_1$, $R_2$ and Y have the meanings indicated in the description), a process for the preparation thereof and pharmaceutical compositions containing them as active ingredient are described.

Compounds of formula I exhibit anto-serotonin activity.

4 Claims, No Drawings

ISOXAZOLE CONTAINING COMPOUNDS EXHIBITING ANTI-SEROTONIN ACTIVITY

The present invention relates to esters and amides of isoxazolcarboxylic acids, and more particularly, it relates to esters and amides of isoxazolcarboxylic acids with alcohols or amines of nitrogen containing heterocycles, to the process for the preparation thereof and to pharmaceutical compositions containing them as active ingredient.

Many compounds as antagonists at receptors for serotonin (hereinafter indicated as 5-HT receptors) have been described in the literature (Goodman and Gilman's - The Pharmacological Basis of Therapeutics - 7th Edition, pages 633-635).

Some of these compounds, and expecially methysergide (Merck Index, 10th Edition, No. 6011, 878-879) and cyproheptadine (Merck Index, 10th Edition, No. 2766, 398-399) have been used in therapy. The discovery of a variety of subtypes of 5-HT receptors, recently classified as 5-$HT_1$, 5-$HT_2$ and 5-$HT_3$ receptors [(Bradly et al., Neuropharmacology, vol. 25, No. 6, pages 563-576, (1986)], directed Research toward compounds possessing a selective antagonist activity at one of the subtypes of 5-HT receptors. Antagonist compound of 5-$HT_3$ receptors are particularly interesting and among them Metoclopramide (Merck Index, 10th Edition, No. 6019, page 880) is one of the first drugs.

Successively, several compounds have been developed, some of which structurally closely related with Metoclopramide, to attempt to single out specific antagonists at 5-$HT_3$ receptors. We mention as examples the compounds described in U.K. patent applications no. 2 125 398 and no. 2 152 049 (Sandoz Ltd). and in European patent application no. 0 201 165 (Beecham Group PLC).

Among these compounds, one of the more promising because under development is 3-endo-tropanyl indol-3-yl carboxylate, better known as ICS 205-903 [Iversen - Nature, vol. 316, pages 107-8, (1985)].

We have now found a new class of compounds having isoxazole structure which are very selective antagonists at 5-$HT_3$ receptors and possess a particularly high pharmacologic activity, expecially as antiarrhythmics, and a lower toxicity.

Therefore, object of the present invention are the compounds of formula

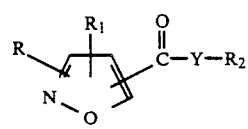
(I)

wherein

R and $R_1$, equal to or different from each other, are hydrogen, $C_1$-$C_3$ alkyl, halogen, $C_1$-$C_3$ alkoxy optionally substituted by one phenyl group or phenyl optionally substituted by from one to three substituents selected from $C_1$-$C_3$ alkyl, halogen, $C_1$-$C_3$ alkoxy;

Y is oxygen or NH;

$R_2$ is a group selected from

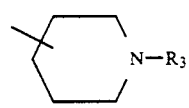
(A)

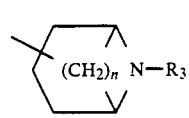
(B)

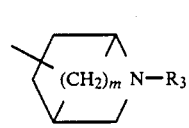
(C)

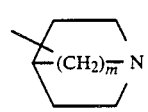
(D)

wherein $R_3$ is a $C_1$-$C_3$ alkyl;

n is an integer selected from 2 and 3 and m is an integer selected from 1, 2 and 3; and pharmaceutically acceptable salts thereof with organic or inorganic acids.

Compounds of formula I are useful in therapy as analgesics, as favouring the gastric motility, as antiemetics and for treating disorders of the nervous system, and expecially disorders of the cardio circulatory system.

Specific examples of compounds of formula I are:

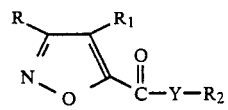

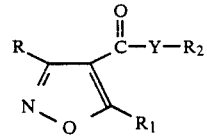

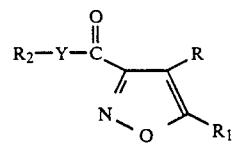

wherein R, $R_1$ and Y have the above reported meanings and $R_2$ is a group selected from:
1-methyl-3-piperidinyl
1-ethyl-3-piperidinyl
1-methyl-4-piperidinyl
1-ethyl-4-piperidinyl
8-methyl-8-azabicyclo[3,2,1]oct-3-yl
9-methyl-9-azabicyclo[3,3,1]non-3-yl
8-methyl-8-azabicyclo[3,2,1]oct-2-yl
9-methyl-9-azabicyclo[3,3,1]non-2-yl
2-methyl-2-azabicyclo[2,2,1]hept-6-yl
2-methyl-2-azabicyclo[2,2,2]oct-6-yl
6-methyl-6-azabicyclo[3,2,2]non-9-yl
2-methyl-2-azabicyclo[2,2,1]hept-5-yl
2-methyl-2-azabicyclo[2,2,2]oct-5-yl
6-methyl-6-azabicyclo[3,2,2]non-8-yl
1-azabicyclo[2,2,1]hept-3-yl 1-azabicyclo[2,2,2]oct-3-yl
1-azabicyclo[3,2,2]non-6-yl optionally salified with pharmaceutically acceptable organic or inorganic acids.

By the term salts of pharmaceutically acceptable acids, addition salts are intended with hydrochloric, hydrobromic, boric, phosphoric, sulfuric, acetic, tartaric, lactic, maleic, citric, succinic, benzoic, 4-hydroxybenzoic, ascorbic, methanesulfonic, alphaketoglutaric and alpha-glycerophosphoric acid as well as salts of the compounds of formula (I) wherein the nitrogen atom of groups (A), (B), (C) and (D) is quaternized with a compound of formula $R_4X$ wherein $R_4$ is a $C_1$-$C_3$ alkyl and X is the anion of a pharmaceutically acceptable acid. Preferred examples of compounds of formula I are those wherein:

R and $R_1$, equal to, or different from each other, are hydrogen, methyl, bromine, chlorine, methoxy, phenyl or benzyloxy;

$R_2$ is 1-methyl-3-piperidinyl, 1-ethyl-3-piperidinyl, 1-methyl-4-piperidinyl, 1-ethyl-4-piperidinyl, 8-methyl-8-azabicyclo-[3,2,1]oct-3-yl, 8-methyl-8-azabicyclo[3,2,1]oct-2-yl or 1-azabicyclo[2,2,2]oct-3-yl.

Preferred examples of salts of the compounds of formula I include addition salts with hydrochloric or hydrobromic acid and salts of quaternized derivatives wherein $R_4$ is methyl and X is the bromide or chloride anion.

It is clear to the man skilled in the art that the compounds of formula I can have one or more asymmetry centers and therefore they can exist in form of stereoisomers. Therefore, object of the present invention are the compounds of formula I as single stereoisomers or as stereoisomeric mixture. Moreover, when $R_2$ is a group (B), (C) or (D), it may be either in an exo or endo form.

Object of the present invention are also the compounds of formula I either as single exo or endo isomers, or as a mixture of isomers. Endo isomers of the compounds of formula I are preferred. Compounds of formula I are prepared by condensing a reactive derivative of an isoxazolecarboxylic acid with an alcohol or an amine of a suitable nitrogen containing heterocycle.

The process for the preparation of the compounds of formula I is a further object of the present invention, it is represented in the following scheme:

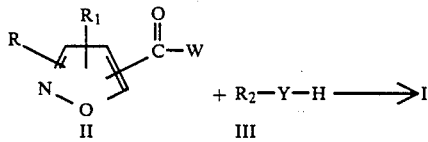

wherein R, $R_1$, $R_2$ and Y have the above reported meanings and the group-CO—W represents the carboxylic function (W=OH) or a reactive derivative thereof such as acyl halides (W=halogen), mixed anhydrides and reactive esters.

Specific examples of reactive derivatives are acyl chlorides and bromides, mixed anhydrides with pivalic acid or with carbonic acid and esters thereof, reactive ester such as esters with hydroxybenzotriazole or hydroxysuccinimide. The reactive derivative of formula II is condensed with an alcohol (Y=O) or an amine (Y=NH) of formula III to afford an ester or an amide of formula I respectively. The condensation reaction is carried out by melting the reaction mixture or by working at temperatures comprised between 0° C. and room temperature in a suitable solvent.

Examples of solvents are halogenated hydrocarbons such as methylene chloride, ethers such as tetrahydrofuran, hydrocarbons such as benzene and toluene or acetonitrile optionally in the presence of a base.

Alternatively, the condensation may be carried out by reacting directly an isoxazole carboxylic acid (W=OH) with the amine of formula III in the presence of a suitable condensation agent like N,N-dicyclohexylcarbodiimide or N,N'-carbonyldiimidazole. Compounds of formula I in form of a single stereoisomer may be prepared according to the above mentioned process using as starting materials the compounds of formula III in the optically active form.

Alternatively, the single stereoisomers may be isolated from the stereoisomeric mixture according to conventional techniques such as crystallization or chromatography. Analogously, starting from a compound of formula III in the endo or exo configuration, the corresponding endo or exo isomers of compounds of formula I are obtained. The salts of the compounds of formula I are prepared according to conventional techniques.

For instance, salts of the compounds of formula I in which the nitrogen atom of groups (A), (B), (C) and (D) is quaternized are prepared from the corresponding base by treatment with an alkyl derivative of formula $$R_4—X$$

wherein $R_4$ and X have the already indicated meanings; in an inert organic solvent, preferably acetone. Compounds of formula II and III are known or can be easily prepared by known methods. Compounds of the present invention are potent highly selective antagonists at 5-$HT_3$ receptors and, as such, they are useful in therapy as analgesics, in particular for the treatment of migraine and trigeminal neuralgia, as favouring the gastric motility, for the treatment of disorders like delayed gastric depletion, dyspepsia and peptic ulcer, for the treatment of obesity, as antiemetics and antidiarrhea in the therapy of carcinoid syndrome. Moreover, they are useful for the treatment of disorders of the central nervous system as antipsychotics, for the treatment of cardiocirculatory diseases and in particular arrythmias.

Compounds of formula I are also useful in the therapy of opiates and nicotine abuse in humans, being also free of sedative effects as well as of effects relating to motility. It is worth noting that the compounds of formula I object of the present invention differ from the known compounds exhibiting antiserotonin activity and in particular from the compounds exhibiting anti 5-$HT_3$ activity in that they are endowed with a higher antiarrhythmic activity, a better tolerability and a higher specificity.

The high selectivity of the compounds of formula I for 5-$HT_3$ receptors has been demonstrated, in comparison with the compound ICS 205-903 (hereinafter indicated as compound R), by evaluating the absence of activity towards other types of receptors. In particular the compounds of formula I proved to be free of anticholinergic and antihistaminic activity (example 6) and free of any affinity for benzodiazepine, $\beta$-adrenergics, $alpha_1$-adrenergics and $Ca^{++}$ receptors (example 8).

The activity at level of 5-$HT_3$ receptors of the compounds of the present invention is evidenced by the absence of affinity for the other subtypes of known serotonin receptors, 5-$HT_1$ and 5-$HT_2$ (example 9) associated with the values obtained in the test of inhibition of the Bezold-Jarisch effect and in the test of serotonin induced inhibition on the nervous potential of fibers C of the rabbit vagus nerve (example 10).

Furthermore, the compounds of formula I do not exhibit any local anaesthetic activity (example 7) contrary to compound R the local anaesthetic activity of which is comparable with that of lidocaine (Merck Index, 10th Edition, No. 5310, page 786). It is known to the man skilled in the art that the local anaesthetic activity is associated, like for lidocaine, with an antiarrythmic activity: the absence of local anaesthetic activity in the compounds of formula I allows to exclude that their antiarrythmic activity is due to this last property.

As we have already pointed out, the compounds of the present invention are potent antagonists at 5-HT$_3$ receptors, particularly active as antiarrythmic agents. From the results of the test of inhibition of arrythmias induced by reperfusion in rat (example 11) it is possible to note that the compounds of formula I are particularly effective in inhibiting ventricular fibrillation and in reducing lethal results and this activity resulted remarkably higher than that of compound R taken as comparison reference. This remarkable antiarrythmic activity has been also confirmed in the inhibition test of noradrenalin induced arrythmias in rat (example 12).

Furthermore, by the Whole-cell patch clamp technique it has been evidenced that the compounds of the present invention are effective in blocking K+ and Na+ channels on heart cells in culture. Compounds of formula I possess also a very good tolerability, better than that of other known compounds exhibiting antiserotonin activity.

In particular, LD$_{50}$ values obtained in the acute toxicity test by oral administration in rat resulted from 2 to 4 times higher than that of the compound R. A further object of the present invention are the pharmaceutical compositions containing a compound of formula I or a pharmaceutically acceptable salt thereof, in admixture with a pharmaceutically acceptable carrier.

Pharmaceutical compositions, prepared according to conventional techniques, may be suitable for the oral or parenteral administration and can be formulated as tablets, coated tablets, capsules, pills, solutions, suspensions, emulsions, suppositories, granules or powders optionally to be dissolved at the time of use. The compositions of the present invention may contain conventional pharmaceutically acceptable excipients such as binders, diluents, lubricants, disintegrating agents, dyes, flavours, wetting agents, surfactants and emulsifiers.

Daily doses of the compound of formula I depend on the treatment type, seriousness and nature of the disease, but they will be generally comprised between 0.001 and 50 mg/kg to be administered in one single dose or more repeated doses. In order to better illustrate the present invention, the following example are now given.

EXAMPLE 1

Preparation of the 3-phenylisoxazole-5-carboxylic acid 3-(endo-8-methyl-8-azabicyclo[3,2,1]octyl) ester hydrochloride (compound No. 1)

Tropine (6.7 g; 46 mmols - containing 3% of water) was dissolved in absolute ethanol (50 ml) and the solution was treated with ethanolic hydrochloric acid in excess. The solution was evaporated to dryness and the residue was treated many times with ethanol until the tropine hydrochloride was obtained as crystals, thereafter ethanol was removed by heating to 40°-50° C. under vacuum, for 30 minutes.

The anhydrous tropine hydrochloride thus prepared was mixed with 3-phenyl-5-isoxazolecarbonylchloride (10.5 g; 50.6 mmoles). The reaction mixture was heated, under agitation, on a previously heated oil bath until complete melting. After 5 minutes the mixture was cooled and the glassy solid obtained was treated with water and ethyl acetate to obtain two clear phases.

The aqueous phase, after washing with ethyl ether, was made alkaline with ammonia and extracted twice with ethyl acetate. The organic extracts were washed with water until neutral pH, dried on sodium sulphate and were evaporated to dryness. 3-phenylisoxazole-5-carboxylic acid 3-(endo-8-methyl-8-azabicy-clo[3,2,-1]octyl) ester (12.7 g), was obtained as crystalline base, which was then dissolved in warm acetonitrile. The solution was acidified with ether containing hydrochloric acid.

The crystalline precipitate was filtered and recrystallized from methanol (200 ml) thus obtaining the hydrochloride of 3-phenylisoxazole-5-carboxylic acid 3-(endo-8-methyl-8-azabicyclo[3,2,1]-octyl)ester (10.9 g, yield 67.9%) with m.p. 271°-273° C. (decomposition).

$^1$H—NMR (200 MHz, CDCl$_3$): delta (ppm): 2.08–2.62 (m, 6H); 2.78 (s, 3H, N—CH$_3$); 3.22 (ddd, 2H, tropin-H-endo); 3.80 (m, 2H, CH—N—CH); 5.46 (dd, 1H, CH—O); 7.32 (s, 1H, CH=C); 7.46–7.85 (m, 5H, arom). By working analogously, the following compounds were prepared:

(3-phenyl-5-methyl)-isoxazole-4-carboxylic acid 3-endo-8-methyl-8-azabicyclo[3,2,1]octyl ester hydrochloride (compound No. 2) yield 55.7% m.p. 219°-221° C. (decomposition)
$^1$H—NMR (200 MHz, CDCl$_3$): delta (ppm): 1.68–2.12 (m, 6H); 2.56–2.59 (2s, 3H, N—CH$_3$); 2.72 (s, 3H, C—CH$_3$); 2.94 (ddd, 2H, tropin-H-endo); 3.52 (m, 2H, CH—N—CH); 5.18 (dd, 1H, CH—O); 7.39–7.53 (m, 5H, arom).

3-benzyloxyisoxazole-5-carboxylic acid 3-(endo-8-methyl-8-azabicyclo[3,2,1]octyl) ester hydrochloride (compound No. 3) yield 9.2% m.p. 209°-211° C. (decomposition)
$^1$H—NMR (200 MHz, CDCl$_3$): delta (ppm): 2.05–2.56 (m, 6H); 2.77–2.74 (2s, 3H, N—CH$_3$); 3.23 (ddd, 2H, tropin-H-endo); 3.77 (m, 2H, CH—N—CH); 5.30 (s, 2H, CH$_2$—O); 5.41 (dd, 1H, CH—O); 6.63—(s, 1H, CH=C); 7.36–7.49 (m, 5H, arom).

3-bromoisoxazole-5-carboxylic acid 3-(endo-8-methyl-8-azabicyclo[3,2,1]octyl) ester hydrochloride (compound No. 4) yield 61.4% m.p. 243°-245° C. (decomposition)
$^1$H—NMR (200 MHz, CDCl$_3$): delta (ppm): 2.05–2.56 (m, 6H); 2.76 (s, 3H, N—CH$_3$); 3.22 (ddd, 2H, tropin-H-endo); 3.76 (m, 2H, CH—N—CH); 5.45 (dd, 1H, CH—O); 7.05 (s, 1H, CH=C).

3-methylisoxazole-5-carboxylic acid 3-(endo-8-methyl-8-azabicyclo[3,2,1]octyl) ester hydrochloride (compound No. 5) yield 53% m.p. 248°-250° C. (decomposition)
$^1$H—NMR (200 MHz, CDCl$_3$): delta (ppm): 2.05–2.56 (m, 6H); 2.38 (s, 3H, C—CH$_3$); 2.76 (s, 3H, N—CH$_3$); 3.18 (ddd, 2H, tropin-H-endo); 3.77 (m, 2H, CH—N—CH); 5.42 (dd, 1H, CH—O); 6.84 (s, 1H, CH=C).

3-methoxyisoxazole-5-carboxylic acid 3-(endo-8-methyl-8-azabicyclo[3,2,1]octyl) ester hydrochloride (compound No. 6) yield 58.6% m.p. 203°–205° C. (decomposition)
$^1$H—NMR (200 MHz, CDCl$_3$): delta (ppm): 2.03–2.53 (m, 6H); 2.74–2.77 (2s, 3H, N—CH$_3$); 3.17 (ddd, 2H, tropin-H-endo); 3.80 (m, 2H, CH—N—CH); 3.99 (s, 3H, CH$_3$O); 5.37 (dd, 1H, CH—O); 6.57 (s, 1H, CH=C).

5-phenylisoxazole-3-carboxylic acid 3-(endo-8-methyl-8-azabicyclo[3,2,1]octyl) ester hydrochloride (compound No. 7) yield 56.1% m.p. 289°–291° C. (decomposition)
$^1$H—NMR (200 MHz, CDCl$_3$): delta (ppm): 2.10–2.68 (m, 6H); 2.78 (s, 3H, N—CH$_3$); 3.18 (ddd, 2H, tropin-H-endo); 3.79 (m, 2H, CH—N—CH); 5.45 (dd, 1H, CH—O); 6.93 (s, 1H, CH=C); 7.45–7.85 (m, 5H, arom).

5-methylisoxazole-3-carboxylic acid 3-(endo-8-methyl-8-azabicyclo[3,2,1]octyl) ester hydrochloride (compound No. 8) yield 61.4% m.p. 256°–258° C. (decomposition)
$^1$H—NMR (200 MHz, CDCl$_3$): delta (ppm): 2.06–2.60 (m, 6H); 2.49 (d, 3H, J=1 Hz, C—CH$_3$), 2.74–2.77 (2s, 3H, N—CH$_3$); 3.22 (ddd, 2H, tropin-H-endo); 3.76 (m, 2H, CH—N—CH); 5.42 (dd, 1H, CH—O); 6.42 (d, 1H, J=1 Hz, CH=C).

5-methylisoxazole-3-carboxylic acid 4-(1-methylpiperidinyl) ester hydrochloride (compound No. 9) yield 54.8% m.p. 219°–221° C. (decomposition)
$^1$H—NMR (200 MHz, CDCl$_3$): delta (ppm): 2.12–3.65 (m, 8H); 2.49 (d, 3H, C—CH$_3$); 2.80 (s, 3H, N—CH$_3$); 5.41 (m, 1H, CH—O); 6.43 (q, 1H, CH=C).

5-methylisoxazole-3-carboxylic acid 3-(1-methylpiperidinyl) ester hydrochloride (compound No. 10) yield 43.4% m.p. 201°–203° C. (decomposition)
$^1$H—NMR (200 MHz, CDCl$_3$): delta (ppm): 1.61–3.74 (m, 8H); 2.47 (d, 3H, C—CH$_3$); 2.90 (s, 3H, N—CH$_3$); 5.61 (m, 1H, CH—O); 6.42 (q, 1H, CH=C).

5-methylisoxazole-3-carboxylic acid 3-(1-azabicyclo[2,2,2]octyl) ester hydrochloride (compound No. 11) yield 15.2% m.p. 246°–248° C. (decomposition)
$^1$H—NMR (200 MHz, CDCl$_3$): delta (ppm): 1.81–2.62 (m, 5H); 2.51 (d, 1H, C—CH$_3$); 3.28–3.84

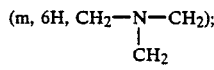

5.35 (m, 1H, CH—O); 6.44 (q, 1H, CH=C).

EXAMPLE 2

Preparation of 5-methylisoxazole-3-carboxylic acid 3-(1-methylpiperidinyl) ester hydrochloride (compound No. 10)

A solution of 5-methyl-3-isoxazolecarbonylchloride (5.33 g; 36.6 mmols) in methylene chloride (15 ml) was poured dropwise into a solution of 3-hydroxy-1-methyl-piperidine (4.21 g; 36.6 mmols) in methylene chloride (50 ml), cooled to 5° C.

After 1 hour at room temperature, the reaction mixture was poured into an aqueous solution of potassium carbonate and the phases were separated. The aqueous phase was extracted with methylene chloride.

The combined organic extracts were washed with water, made anhydrous and evaporated under vacuum.

The residue (8 g) was crystallized from isopropyl ether/petroleum ether (ratio 1:3; 80 ml) thus obtaining 5-methylisoxazole-3-carboxylic acid 3-(1-methyl-piperidinyl) ester (4.7 g; yield 49.3%); m.p. 59.3°–61.5° C.

By dissolution in acetonitrile (30 ml) and diethyl ether (30 ml) followed by acidification with hydrochloric acid in ether, the 5-methylisoxazole-3-carboxylic acid 3-(1-methylpiperidinyl) ester hydrochloride was obtained (4.37 g; yield 45.8%) showing the same characteristics as the sample obtained as described in example 1. By working analogously, the following compound was prepared:

5-methylisoxazole-3-carboxylic acid 4-(1-methylpiperidinyl) ester hydrochloride (compound No. 9) yield 81% m.p. 219°–221° C. (decomposition)
The spectroscopic characteristics of the compound were identical to those of the sample obtained as described in example 1.

3-ethyl-5-methylisoxazole-4-carboxylic acid 3-(endo-8-methyl-8-azabicyclo[3,2,1]octyl) ester hydrochloride (compound 12) yield 29.1% m.p. 263°–265° C.
$^1$H—NMR (200 MHz, CDCl$_3$): delta (ppm): 1.21 (t, 3H, J=7.5 Hz, CH$_2$—CH$_3$); 2.03–2.11 (m, 2H); 2.20–2.31 (m, 4H); 2.58 (s, 3H, CH$_3$—C); 2.73 (d, 3H, CH$_3$—N); 2.78 (q, 2H, J=7.5 Hz, CH$_2$—CH$_3$); 3.05–3.18 (m, 2H); 3.79 (m, 2H, CH—N—CH); 5.20 (m, 1H, COOCH); 12.35 (broad s, 1H, HCl).

3-propyl-isoxazole-5-carboxylic acid 3-(endo-8-methyl-8-azabicyclo[3,2,1]octyl) ester hydrochloride (compound No. 13) yield 29.1% m.p. 238°–240° C.
$^1$H—NMR (200 MHz, CDCl$_3$): delta (ppm): 0.85 (t, 3H, J=7.5 Hz, CH$_3$—CH$_2$—CH$_2$); 1.68 (sextet, 2H, J=7.5 Hz, CH$_3$—CH$_2$—CH$_2$); 2.53–2.94 (m, 6H); 2.67 (t, 2H, J=7.5 Hz, CH$_3$—CH$_2$—CH$_2$); 2.75 (d, 3H, CH$_3$—N); 3.12–3.25 (m, 2H); 3.40 (m, 1H, COOCH); 3.73–3.83 (m, 2H, CH—N—CH); 6.83 (s, 1H, H isoxazole); 12.53 (broad s, 1H, HCl).

EXAMPLE 3

Preparation of N-(1-ethyl-3-piperidinyl)-5-methylisoxazole-3-carboxamide (compound No. 14)

To a solution of 3-amino-N-ethylpiperidine (4.61 g; 36 mmols) in methylene chloride (20 ml) and water (10 ml), a solution of 5-methyl-3-isoxazole-carbonyl chloride (5.68 g; 39 mmols) in methylene chloride (35 ml) and 1N NaOH (39 ml) were added contemporaneously at the temperature of 3° C.

After 30 minutes the temperature was allowed to raise to the room value and after 1–3 h the phases were separated; the aqueous phase was extracted again with methylene chloride.

After drying and evaporation of the solvent, a crude product (7.1 g) was obtained which was then crystallyzed from a mixture of isopropyl ether/petroleum ether (ratio 1:1; 160 ml).

N-(1-ethyl-3-piperidinyl)-5-methylisoxazole-3-carboxamide was obtained (4.3 g; yield 50.3%) m.p. 84°–86° C.

$^1$H—NMR (200 MHz, CDCl$_3$): delta (ppm): 1.04 (t, 3H, CH$_3$—CH$_2$); 1.51–2.61 (m, 8H); 2.38 (q, 2H, CH$_3$—CH$_2$); 2.46 (d, 1H, CH$_3$—C); 4.20 (m, 1H, CH—N); 6.41 (q, 1H, CH=C); 7.29 (d, 1H, NH). By working analogously the following compounds were prepared:

N-[3-(exo-8-methyl-8-azabicyclo[3,2,1]octyl)]-5-methylisoxazole-3-carboxamide (compound No. 15) yield 27.5% m.p. 156°–158° C.

$^1$H—NMR (200 MHz, CDCl$_3$): delta (ppm): 1.52–2.07 (m, 8H); 2.26 (s, 3H, N—CH$_3$); 2.43 (d, 3H, CH$_3$—C); 3.16 (m, 2H, CH—N—CH); 4.24 (m, 1H, CH—NHCO); 6.38 (q, 1H, CH=C); 6.50 (d, 1H, NH).

N-[3-(endo-8-methyl-8-azabicyclo[3,2,1]octyl)]-5-methylisoxazole-3-carboxamide (compound No. 16) yield 23.4% m.p. 62°–70° C. (contains 10% of exo isomer)

$^1$H—NMR (200 MHz, CDCl$_3$): delta (ppm): 1.61–2.31 (m, 8H); 2.27 (s, 3H, N—CH$_3$); 2.46 (d, 3H, CH$_3$—C); 3.16 (m, 2H, CH—N—CH); 4.22 (m, 1H, CHNHCO); 6.42 (q, 1H, CH=C); 7.19 (d, 1H, NH).

EXAMPLE 4

Preparation of N-[3-(1-azabicyclo[2,2,2]octyl)]-5-methylisoxazole-3-carboxamide (compound No. 17)

A solution of 5-methyl-3-isoxazolecarbonylchloride (3.93 g; 27 mmols) in tetrahydrofuran (24 ml) and 1N NaOH (27 ml) were added at the same time to a solution of 3-aminochinuclidine dihydrochloride (3.25 g; 16.32 mmols) in tetrahydrofuran (THF) (30 ml) and 1N NaOH (32.7 ml) cooled to 3° C.

Additions were performed in such a manner to keep the temperature of the reaction mixture below 5° C. and the pH around 9-10.

After 30 minutes the temperature was allowed to raise up to the room value; after standing overnight the phases were separated and aqueous phase was extracted twice with THF after having further made it alkaline with concentrated NaOH.

Organic extracts were combined and dried; the solvent was evaporated to residue thus obtaining a crude product (3.6 g) which was crystallized from t.butylmethylether (70 ml).

N-[3-(1-azabicyclo[2,2,2]octyl)]-5-methylisoxazole-3-carboxamide was obtained (2.3 g; yield 60%) m.p. 108°–110° C.

$^1$H—NMR (200 MHz, CDCl$_3$): delta (ppm): 1.39–1.82 [m, 4H, (CH$_2$)$_2$CHCHN]; 1.99 (m, 1H, CH tert.); 2.47 (d, 3H, CH$_3$—C); 2.52–2.63 (m, 1H) 2.68–2.96 [m, 4H, (CH$_2$)$_2$NCH$_2$CHN]; 3.32–3.46 (m, 1H, N—CHH—CHN); 4.10 (m, 1H, CH—NHCO); 6.42 (q, 1H, CH=C); 6.92 (d, 1H, NH).

EXAMPLE 5

Preparation of endo-8,8-dimethyl-3-(5-methylisoxazole-3-carbonyloxy)-8-azoniabicyclo[3,2,1]octane bromide (compound No. 18)

3-(endo-8-methyl-8-azabicyclo[3,2,1]octyl) ester of 5-methylisoxazole-3-carboxylic acid (7.09 g; 28.33 mmols), prepared as described in example 1, was treated with a solution of methyl bromide (6.7 g; 70.8 mmols) in acetone (100 ml).

A product separates and after 16 hours the crystalline precipitate was filtered under vacuum and washed with acetone.

After drying under vacuum endo-8,8-dimethyl-3-(5-methylisoxazole-3-carbonyloxy)-8-azoniabicyclo[3,2,1]octane bromide was obtained (9.4 g; yield 96.1%) m.p. 290°–292° C.

$^1$H—NMR (200 MHz, DMSO-d$_6$): delta (ppm): 2.04–2.72 (m, 8H); 2.51 (d, 3H, CH$_3$—C); 3.10 (s, 3H, CH$_3$—N$^+$); 3.20 (s, 3H, CH$_3$—N$^+$); 3.95 (m, 2H, CH—N—CH); 5.29 (m, 1H, CH—O); 6.72 (q, 1H, CH=C).

EXAMPLE 6

Preparation of 5-ethyl-isoxazole-3-carboxylic acid 3-(endo-8-methyl-8-azabicyclo[3,2,1]octyl) ester hydrochloride (compound No. 20)

A solution of 5-ethyl-isoxazole-3-carbonyl chloride (15.58 g; 97.6 mmols) in acetonitrile (100 ml) was added dropwise at room temperature to a solution of anhydrous tropine hydrochloride (17.41 g; 98 mmols) in acetonitrile (300 ml).

After 5 hours, a solution of triethylamine (27.3 ml; 196 mmols) in actonitrile (50 ml) was added dropwise at 5° C.

A 24 hours thereafter, the reaction mixture was worked up in a way analogous to that described in example 2 to obtain the desired product which was crystallized from t.butyl-methyl-ether and acetonitrile (1:1).

Compound no. 20 (5.38 g; yield 18.3%) was obtained. m.p. 249°–251° C.

$^1$H—NMR (200 MHz, CDCl$_3$): delta (ppm): 1.27 (t, 3H, J=7.5, CH$_3$CH$_2$); 2.02–2.13 (m, 2H); 2.20–2.57 (m, 4H, CH—CH$_2$—CH$_2$—CH); 2.73 (d, 3H, J=5, CH$_2$N); 2.78 (dq, 2H, J=7.5, J$^2$=0.8, CH$_2$—CH$_3$); 3.06–3.20 (m, 2H); 3.73–3.80 (m, 2H, CH—N—CH); 3.63 (m, 1H, COO—CH); 6.37 (t, 1H, J$^2$=0.8 H-isoxazole); 12.42 (broad s, 1H, HCl).

By operating according to this procedure, the following compound was prepared too:

5-isoxazole-carboxylic acid 3-(8-methyl-8-azabicyclo[3,2,1]octyl) ester hydrochloride (compound No. 21) yield 17.1% m.p. 204°–206° C. (decomposition)

$^1$H—NMR (200 MHz, CDCl$_3$): delta (ppm): 2.06–2.57 (m, 6H); 2.76 (d, 3H, J=5, CH$_3$N); 3.17–3.28 (m, 2H); 3.75–3.83 (m, 2H, CH—N—CH); 5.43 (m, 1H, COO—CH); 7.02 (d, 1H, J=1.8, 4H-isoxazole); 8.38 (d, 1H, J=1.8 3H-isoxazole); 12.63 (broad s, 1H, HCl).

EXAMPLE 7

Preparation of 3-bromo-5-methyl-isoxazole-4-carboxylic acid 3-(endo-8-methyl-8-azabicyclo[3,2,1]octyl) ester hydrochloride (compound No. 22)

A solution of N,N-dicyclohexyl-carbodiimide (4.539 g; 22 mmols) in methylene chloride (20 ml) was added dropwise at room temperature to a solution of anhydrous tropine hydrochloride (3.91 g; 22 mmols), 3-bromo-5-methyl-isoxazole-4-carboxylic acid (4.12 g; 20 mmols) and 4-pirrolidinopiridine (0.303 g; 2 mmol) in methylene chloride (250 ml).

After 24 hours, the reaction mixture was filtered and the precipitate was washed with hydrochloric acid at 5% concentration. The filtrate was extracted twice with 5% hydrochloric acid. The hydrochloric solutions were combined and made alkaline (pH 8.5) with solid $K_2CO_3$ and the solid separated was extracted with methylene chloride.

After evaporation of the solvent the oily residue was treated with warm n.heptane.

The residue was dissolved in diethylether and acidified with HCl in ether.

The white solid precipitate was collected by filtration and crystallized from acetonitrile to yield the desired product (1.67 g; yield 22.8%).

m.p. 194°–916° C. (decomposition)

$^1$H—NMR (200 MHz, $CDCl_3$): delta (ppm): 2.10–2.52 (m, 6H); 2.70 (s, 3H, $CH_3C$); 2.74 (d, 3H, J=5.3, $CH_3N$); 3.01–3.23 (m, 2H); 3.74–3.80 (m, 2H, CH—N—CH); 5.30 (m, 1H, COO—CH); 12.40 (broad s, 1H, HCl).

EXAMPLE 8

Preparation of 3-isoxazole-carboxylic acid 3-(endo-8-methyl-8-azabicyclo[3,2,1]octyl) ester hydrochloride (compound No. 23)

To a solution of imidazole (2.84 g; 41.66 mmols) in tetrahydrofuran (THF) (28 ml), a solution of 3-isoxazole-carbonyl chloride (2.74 g; 20.83 mmols) in THF was added and the mixture was left to stand at room temperature for 40 hours.

After filtration, anhydrous tropine (2.64 g; 18.70 mmols) and, after 2 hours, a solution of imidazole-sodium in THF (0.25 ml) were added to it.

[The imidazole sodium solution was prepared by dissolving metal sodium (0.67 g) in a solution of imidazole (6.8 g) in THF (68 ml)].

After 3 days the solvent was removed at reduced pressure and the residue was collected with methylene chloride and diluted hydrochloric acid.

The reported aqueous phase was made alkaline (pH 8.5) and extracted with methylene chloride.

The organic phases collected together were dried and evaporated at reduced pressure. The crystalline residue was dissolved in diethylether and acidified by HCl in ether.

The crystalline precipitate was collected by filtration. Compound No. 23 (2.72 g; yield 53.4%) was obtained.

m.p. 260°–262° C.

$^1$H—NMR (200 MHz, $CDCl_3$): delta (ppm): 2.00–2.60 (m, 6H); 2.74 (d, 3H, J=5, $CH_3N$); 3.10–3.20 (m, 2H); 3.75–3.81 (m, 2H, CH—N—CH); 5.40 (m, 1H, COO—CH); 6.77 (d, 1H, J=1.7, 4H-isoxazole); 8.53 (d, 1H, J=1.7, 5H-isoxazole); 12.37 (broad s, 1H, HCl).

EXAMPLE 9

Preparation of 5-propyl-isoxazole-3-carboxylic acid 3-(endo-8-methyl-8-azabicyclo[3,2,1]octyl) ester hydrochloride (compound No. 24)

The compound was prepared by reacting 5-propyl-3-isoxazole carboxylic acid (5.76 g; 36.9 mmols) with anhydrous tropine (5.21 g; 36.9 mmols) in THF according to the procedure of example 7 but in place of N,N-dicyclohexylcarbodiimide, N,N-carbonyldiimidazole (7.18 g; 44.37 mmols) was used.

Work-up of the reaction mixture and treatment with HCl in ether afforded the desired product (7.01 g; yield 60.4%).

m.p. 203°–205° C.

$^1$H—NMR (200 MHz, $CDCl_3$): delta (ppm): 0.94 (t, 3H, J=7.5, $CH_3$—$CH_2$—$CH_2$); 1.70 (sextet, 2H, J=7.5, $CH_3$—$CH_2$—$CH_2$); 2.01–2.60 (m, 6H); 2.74 (d, 3H, J=5.1, $CH_3N$); 2.74 (t, 2H, J=7.5, $CH_2$—$CH_2$—$CH_3$); 3.07–3.20 (m, 2H); 3.73–3.80 (m, 2H, CH—N—CH); 5.37 COO—CH); 6.37 (s, 1H, H-isoxazole); 12.42 (broad s, 1H, HCl).

Pharmacological Part

EXAMPLE 10

Determination of the anticholinergic and antihistaminic activity in vitro

Guinea pigs of both sexes, weighing about 400 g, were sacrified by cervical dislocation.

Segments measuring 5–6 cm were drawn form the end portion of the small intestine and placed into a bath for isolated organs at 37° C.

The antagonist activity of the compounds of formula I and of compound R was evaluated by determining the contracturing effect of acetylcholine and histamine both in the absence and in the presence of said compounds.

Acetylcholine and histamine were added to the bath in increasing doses until a maximum response was obtained.

Contracturing responses were defined by means of an isotonic transducer and a Brush poligraph.

Test compounds were added to the bath in such a dosage as to reach a fixed concentration equal to $10^{-5}M$.

Antagonist properties ($pA_2$) of some compounds of formula I and of compound R with respect to acetylcholine and histamine are reported in table 1 and table 2 respectively.

TABLE 1

Antichlonergic activity ($pA_2$) of the compounds of formula I and of compound R in comparison with atropine.

| Compound | 3 | 5 | 6 | 8 | 9 | 10 | 11 | 16 | 18 | R | Atropine |
|---|---|---|---|---|---|---|---|---|---|---|---|
| $pA_2$ |  | 5.7 | 4.5 | 4.9 | 5.2 | 4.6 | 4.3 | 5.3 | 3.9 | 5.2 4.8 | 9.1 |

TABLE 2

Antihistaminic activity (pA$_2$) of the compounds of formula I and of compound R in comparison with pyrilamine.

| Compound | 3 | 5 | 6 | 8 | 9 | 10 | 11 | 14 | 15 | 16 | 17 | 18 | R | Pyrilamine |
|---|---|---|---|---|---|---|---|---|---|---|---|---|---|---|
| pA$_2$ | 5.6 | 4.9 | 5.2 | 5.2 | 5.0 | 3.7 | 5.5 | 3.5 | 4.3 | 5.1 | 4.3 | 4.8 | 5.5 | 9.4 |

The pA$_2$ values reported in table 1 and table 2 show that the compounds of formula I of the present invention and compound R are practically free of anticholinergic and antihistaminic activity.

EXAMPLE 11

Evaluation of the local anaesthetic activity in vivo and in vitro (a) Evaluation of the local anaesthetic activity on sciatic nerve preparation in comparison with lidocaine.

Male albino rats weighing 350–400 g, narcotized with urethan (1.5 g i.p.) were used.

Sciatic nerves, isolated and deprived of epineurium under binocular observation, were singly transferred into a special three compartmentalized chamber according to the method described by Bowman et al. in Textbook of Pharmacology, Blackwell Scientific Publications 1982.

The nerve was electrically stimulated with overmaximal single shocks (12 V, 0.1 m sec., 0.2 Hz).

The action potential obtained was visualized on storage osciloscope. After having established the height of the action potential of the control, its changes were evaluated within first 30 seconds and at every minute after the application of the Ringer's solution (in mmols: NaCl 147; KCl 2.7; CaCl$_2$ 1.8; glucose 5.5) medicated with the test compound.

This solution was kept in contact with the nerve for the time necessary to reach the highest inhibition for every given concentration (8 minutes).

The ED$_{50}$ of the compounds of formula I, of compound R and of lidocaine were calculated on the base of the percentage of inhibition determined for at least three different concentrations of the test compounds.

Values of ED$_{50}$ are reported in the following table 3.

TABLE 3

Values of ED$_{50}$ (mM) of some compounds of di formula I and of compound R in comparison with lidocaine in the local anaesthesia test on the rat sciatic nerve in vitro.

| Compound | ED$_{50}$ (C.L. 95%) mM |
|---|---|
| R | 1.3 (1.2–1.5) |
| 6 | >15 |
| 8 | >15 |
| 9 | >15 |
| 10 | >15 |
| 11 | >15 |
| 18 | >15 |
| lidocaine | 0.6 (0.5–0.7) |

The results reported in the table show that the compounds of the present invention are practically free of local anaesthetic activity in contrast with compound R the good activity of which was evidenced by the comparison with lidocaine.

(b) Evaluation of the local anaesthetic activity in the test of the guinea pig back in vivo in comparison with lidocaine.

The local anaesthetic activity was evaluated by the method of intracutaneous infiltration in the guinea pig back as described by Bulbring E. and Wajda I. [(J. Pharmacol. Exp. Ther. 85, 78, (1945)].

Female guinea pigs weighin 400–500 g were treated intracutaneously in 4 points of their back.

At 5 minutes intervals, it was determined the reactivity of the animal to pain in each area by considering the number of responses to 6 pain stimulations.

Compounds of formula I, compound R and lidocaine, dissolved at different concentration in physiological solution adjusting the pH at 7 by addition of NaHCO$_3$ were injected under the skin at the constant volume of 0.25 ml.

The distribution of the treatments in the 4 areas of the back was carried out according to the scheme of the Latin square. Experiments were carried out in blind.

As an example, the ED$_{50}$ values for compound No. 8, compound R and lidocaine determined at 5, 15 and 30 minutes after the administration are reported in table 4.

TABLE 4

Values of ED$_{50}$ (mM) of compound No. 8 and of compound R as compared with lidocaine in the test of cutaneous anaesthesia of the guinea pig back.

| | ED$_{50}$ (C.L. 95%) mM | | |
|---|---|---|---|
| Compound | 5 min. | 15 min. | 30 min. |
| R | 2.5 (2.1–2.9) | 3.3 (3.0–3.7) | 5.7 (5.2–6.2) |
| 8 | 28.4 (25.5–31.8) | 32.8 (30.5–35.2) | 41.2 (38.8–43.7) |
| lidocaine | 5.8 (4.9–6.8) | 7.6 (6.8–8.4) | 15.2 (13.8–16.6) |

Values reported in the table confirm that the compound No. 8, representative of the class of the compounds of formula I, is undoubtedly less active as local anaesthetic than compound R and lidocaine.

EXAMPLE 12

Evaluation of the displacement ability for some radioligands in receptor preparations from rat brain (a) Specific binding of $^3$H-flunitrazepam to receptors for benzodiazepins in membranes preparations from rat cerebral cortex. The preparation of receptor membranes was performed using the procedure described by Williamson et al., [(Life Sci., 23, 1535–40, (1978)].

Cerebral cortices of male Spague-Dawley rats weighing about 200 g were homogenized in TRIS-citrate buffer (50 mM; pH 7.1) by means of an Ultra Turrax homogenizer.

After 2 centrifugations at 48.000 rpm for 30 minutes with intermediate rehomogenation of the pellet in the same buffer, the final pellet was suspended until the protein concentration of 3 mg/ml was reached.

The evaluation of the displacement ability of the compounds of formula I, of compound R and Diazepam as comparison substance was carried out by the method described by Braestrup and Nielsen [(J. Neurochem. 37, 333–341, (1981)]; the incubation system was consisting of 1 ml of buffer containing 0.5 mg of protein and $^3$H-flunitrazepam 1 nM both in the absence and in the presence of Diazepam 10$^{-5}$M to determine the nonspecific binding. After incubation for 30 minutes at 4° C., the reaction was ceased by filtration through Whatman GF/B filters and the radioactivity present was counted by liquid scintillation (scintillation mixture: Filtercount - 15 ml; Packard Tri-Carb 4055 scintillatior) with an effectiveness of about 60%. Displacement activity data at level of benzodiazepin receptors for some compounds of formula I representative of the class and of compound R as compared to Diazepam are reported in table 5.

(b) Specific binding of $^3$H-dihydroalprenolol to β-adrenergic receptors in membranes preparations from rat cerebral cortex. The evaluation of the ability of binding to β-receptors prepared from rat cortex membranes was carried out as described by U'Prichard et al. [(J. Biol. Chem. 253, 5090–5102, (1978)]. The preparation of membranes was carried out as described at the preceding point, using buffer TRIS-HCl (50 mM; pH 7.4). The incubation system consisted of homogenate (1 mg protein/ml buffer) and of 1 nM $^3$H-dihydroalprenolol both in the absence and in the presence of isoproterenol $10^{-5}$M to determine the nonspecific binding. After incubation at 25° C. for 20 minutes, the samples were filtered off through Whatman GF/B filters and washed 4 times with 4 ml of buffer. The radioactivity was recorded as described at the preceding point. Data of the displacement activity at level of β-adrenergic receptors for some compound of formula I representative of the class and for the compound R as compared to isoproterenol are reported in table 5.

(c) Specific binding of $^3$H-prazosin to alpha$_1$-adrenergic receptors in membranes preparations from rat cerebral cortex. The ability of binding to alpha$_1$-adrenergic receptors was evaluated by the method described for β-adrenergic at point b. The inoculation system consisted of homogenate of cerebral cortex of rat (2 mg protein/ml buffer) and of $^3$H-prazosin 0.5 nM both in absence and in the presence of norepinephrine $10^{-4}$M. After 20 minutes of incubation at 20° C., the samples were filtered off, washed 3 times with 5 ml of buffer and the radioactivity was counted. Displacement activity data at level of alpha$_1$-adrenergic receptors for some compounds of formula I representative of the class and for compound R in comparison with norepinephrine are reported in table 5.

(d) Specific binding of $^3$H-nitrendipine to Ca$^{++}$ receptors. The displacement ability of the compounds of formula I and of compound R on the specific binding of $^3$H-nitrendipine (1 nM) in preparations of brain receptors membranes of rat was evaluated using the methods described by Murphy e Snyder [(Eur. J. Phar., 77, 201–202, (1982)] either as far as preparations of membranes or receptor dosage was concerned. Displacement activity data at level of Ca$^{++}$ for some compounds of formula I representative of the class and for compound R in comparison with nifedipine are reported in table 5.

TABLE 5

Displacement activity of the compounds No. 5 and No. 8 and of compound R at level of benzodiazepine receptors, β-adrenergics, alpha-adrenergics and Ca$^{++}$ receptors on radioligands in preparations of cerebral cortex membranes of rat.[1]

| Compound | Benzodiazepin receptors $^3$H-flunitrazepam 1nM | β-adrenergic receptors $^3$H-dihydroalprenolol 1nM | α$_1$-adrenergic receptors $^3$H-prazosin 1nM | Receptors of Ca$^{++}$ $^3$H-nitrendipine 1nM |
|---|---|---|---|---|
| 5 | inactive | inactive | inactive | inactive |
| 8 | inactive | inactive | inactive | inactive |
| R | 1,000 | inactive | inactive | inactive |
| diazepam | 4 | | | |
| isoproterenol | | 250 | | |
| norepinephrine | | | 900 | |
| nifedipine | | | | 1.2 |

Data reported in table 5 show that the compounds of formula I, object of the present invention, do not exhibit any affinity for benzodiazepine receptors, β-adrenergic receptors, alpha$_1$-adrenergic receptors and Ca$^{++}$ receptors.

EXAMPLE 13

Evaluation of the affinity for 5-HT$_1$ and 5-HT$_2$ receptors in preparations of membranes from frontal cortex of rat (a) Specific binding of $^3$H serotonin to 5-HT$_1$ receptors. The evaluation of the binding ability of the compounds of formula I and of compound R to 5-HT$_1$ receptors prepared from membranes of rat cortex was carried out as described by Perovtka and Snyder in Molecular Pharmacology, 16, 687–699, (1979). Cerebral cortices of male Sprague-Dawley rats weighing about 200 g were homogenized in TRIS-HCl buffer (50 mM-pH 7.5), CaCl$_2$ (4 mM), Pargyline (10 μM) and ascorbic acid (0.1%) using an Ultra Turrax homogenizer. After 3 centrifugations at 48000 rpm for 15 minutes, the final pellet was suspended again in the same buffer at the protein concentration of 2 μg/ml. The incubation system consisted of buffer (1 mg protein/ml buffer) and $^3$H-serotonin (5 nM) both in absence and in the presence of serotonin (300 nM) and spiroperidol (30 nM) for defining the non specific binding. After 20 minutes of incubation at 37° C., the samples were filtered, washed 3 times with 5 ml of buffer and the radioactivity was counted. Displacement activity data at level of 5-HT$_1$ receptors for some compounds of formula I representative of the class and for compound R in comparison with ketanserine are reported in table 6.

(b) Specific binding of $^3$H-spiroperidol to 5-HT$_2$ receptors. The evaluation of the binding ability of the compounds of the formula I and of compound R to 5-HT$_2$ receptors prepared from rat cortex membranes was carried out as described by Creese and Snyder in Eur. J. Pharm., 49, 201–202, (1978). The cerebral cortex of Sprague-Dawley male rats weighing about 200 g were homogenized in TRIS-HCl (50 nM-pH 7.5). After 2 centrifugations at 48.000 rpm for 15 minutes with intermediate resuspension of the pellet in the same buffer, the membranes were suspended in TRIS-HCl buffer (50 mM-pH 7.5), NaCl (120 mM), KCl (5 mM), CaCl$_2$ (1 mM), MgCl$_2$ (1 mM), ascorbic acid (0.1%) and Pargyline (10 μM) at protein concentration of 1.5 mg/ml. The incubation system consisted of buffer (0.75 mg protein/ml buffer) and $^3$H-spiroperidole (0.25 nM) in the absence or in the presence of ketanserin (6 μM) for the evaluation of nonspecific binding. After 20 minutes of incubation at 37° C., samples were filtered, washed three times with 5 ml of buffer and the radioactivity was counted. The displacement activity data at level of 5-HT$_2$ receptors for some compounds of formula I representative of the class and for compound R in comparison to ketanserine are reported in Table 6.

TABLE 6

Affinity (IC$_{50}$) of some compounds of formula I and of compound R to 5-HT$_1$ and 5-HT$_2$ receptors in preparation of frontal cortex membranes of rat.

| Compound | 5-HT$_1$ | 5-HT$_2$ |
|---|---|---|
| 8 | inactive | inactive |
| 10 | inactive | inactive |
| 18 | inactive | inactive |
| R | inactive | 25 |
| ketanserine | 10 | 0.010 |

EXAMPLE 14

Evaluation of the 5-HT$_3$ activity in vivo and in vitro (a) Evaluation of the anti-5-HT$_3$ activity in vivo by the method of the inhibition of the Bezold-Jarisch effect. The followed method was described by Fozard J. R. et al. [Nature, 316, 126–131, (1985)]. Male albino rats weighing 300–400 g anaesthetized with urethan (1.25–1.5 g/kg i.p.) were used. A tracheal cannula to allow respiration, one little catheter implanted into the jugular vein for administering serotonin and another into the right femoral vein for the intravenous administration of the compounds of formula I and of compound R were used. The bolus injection into the jugular vein of a serotonin solution caused an abrupt reduction of the heart rate quantified as 100% of the effect. The evaluation of the anti-5-HT$_3$ activity was performed by calculating ED$_{50}$ values ($\mu$g/kg) to the antagonism of the heart rate fall. The ED$_{50}$ values obtained for compounds of formula I were comprised between 0.8 and 64 $\mu$g/kg and, under the same experimental conditions, the compound R showed an ED$_{50}$ equal to 6 $\mu$g/kg.

(b) Evaluation of the anti-5-HT$_3$ activity in vitro on the vagus nerve of rabbit. Male albino New Zeland rabbits weighing about 3 kg were sacrificed by an air injection in the edge auriculaers vein. The two vagus nerves, drawn as soon as possible, were placed in a bath of Locke solution having the following composition: 154 mM NaCl; 5.5 mM KCl; 2.2 mM CaCl$_2$; 5 mM glucose; 8 mM TRIS, the pH being adjusted at 7.6 by addition of HCl. Nerves were stripped of their epineurium and transferred into a device described by Kosterlitz H. W. et al., [J. Physiol., 183, IP-3P, (1966)] consisting of four compartments separated by means of 3 elastic membranes having a little hole through which the nerve passes. The glucose concentration perfusing a portion of the nerve was 315 mM. The overmaximal electric stimulation by a single shock at 10 seconds intervals elicited a potential visualized on a storage oscilloscope. In the potential the complexes due to the excitation of fibers A, B and C were distinguished. A serotonin solution applied to the nerve causes the dose-dependent fall of the potential for fibers C only. The non variation of the A-B complex when applying serotonin and the test compounds of formula I indicates on one hand the specific action of the substances for receptors relating to fibers C only (5-HT$_3$ receptors) and on the other hand the absence of local-anaesthetic activity. Tests were performed at room temperature (24°–25° C.). The optimum maximum reduction of the potential of fibers C by serotonin resulted to be 44%. This reduction was adopted as maximum effect (100%). For each nerve a dose-response curve was constructed with cumulative doses of serotonin. After having washed serotonin and recovered the initial potential, the nerve was balanced with a fixed concentration of the compound of formula I for 60 minutes and successively the dose-response curve to serotonin was repeated, the compound of formula I being always present in the same concentration. After having applied a serotonin concentration sufficient to produce the highest effect, the preparation was washed and thereafter it was balanced again for 60 minutes with a solution of the same compound of formula I having a higher concentration. The procedure was then repeated. For each dose of the compound of formula I the test was repeated more than 5 times. The negative natural logarithm of the molar concentration of the compound of formula I which gives a 50% reduction of the effect of the agonist substance (pA$_2$) was calculated. In table 7, the pA$_2$ values of some compounds of formula I are reported.

TABLE 7 pA$_2$ values of some compounds of formula I determined in vitro on the isolated vagus nerve of rabbit.

| Compound | 5 | 6 | 8 |
|---|---|---|---|
| pA$_2$ | 8.8 | 8.9 | 9.2 |

EXAMPLE 15

Inhibitory activity of reperfusion induced arrythmias in rat

Male Sprague-Dawley rats, fasting since at least 16 hours, weighing 300–500 g, were anaesthetized with pentobarbital (60 mg/kg i.p.) and artificially ventilated according to the following parameters: 2 ml/100 g body weight and 54 acts/min. [Clark et al., J. Pharmacol. Methods, 3, 357–368, (1980)]. The implanted catheter in left carotid artery served to monitor the pressure. An EGC in II derivation was recorded and was visualized continuously on oscilloscope. The ligation of the anterior coronary artery was performed according to the method described bySelye H. et al. [Angiology II, 398–407, (1960)]. Before the ligation of the coronary arteries a 15 minutes stabilization period was observed: animals showing a clear hypotension (less than 60 mmHg) were discarded. After 5 minutes the occlusion was removed thus allowing the coronaric flow to restore [Manning A. J. et al., Cardiol. 16, 495–517, (1984)]. Compounds of formula I and compound R were administered directly into the stomach by means of a little probe, 30 minutes before the reperfusion in rats. The analysis of the EGC was performed by evaluating the percentage incidence of two events: dead and ventricular fibrillation (VF). Statistical differences between the control groups, treated with a 0.9% saline solution and the groups of animals treated were evaluated by the $X^2$ test. As example we report in table 8 the results obtained for the compound No. 8 administered per os at doses of 1 mg/kg and 3 mg/kg respectively and for the compound R administered per os at the dose of 3 mg/kg.

TABLE 8

Inhibitory activity of compound No. 8 and of compound R, administered per os, against reperfusion induced arrythmias in rat.

| Treatment | Treated rats | incidence VF | % VF | incidence dead | % dead |
|---|---|---|---|---|---|
| saline (0,5 ml/100 g) | 20 | 17 | 85 | 6 | 30 |
| compound No. 8 (1 mg/kg) | 10 | 2** | 20 | 1 | 10 |
| compound No. 8 (3 mg/kg) | 10 | 0*** | 0 | 0 | 0 |
| compound R (3 mg/kg) | 10 | 7 | 70 | 3 | 30 |

Notes to the table:
VF — ventricular fibrillation
**significance < 0.02
***significance < 0.001

The results reported in the table show that compound No. 8, representative of the class of compounds of formula I of the present invention, was active in the test of reperfusion-induced arrythmias, in particular in inhibiting ventricular fibrillations and in reducing lethal results.

EXAMPLE 16

Inhibition of norepinephrine induced arrythmias in rat.

Male rats, weighing 300–400 g, narcotized with urethan (1.5 g/kg, i.p.) were used; one little probe was implanted into the jugular vein and another into the femoral vein for administering norepinephrine and the test substance respectively. The EGC was recorded in II derivation and from it the instantaneous heart rate was derived. Furthermore, the EGC wave was monitored on oscilloscope and made audible by mean of a loudspeaker. Norepinephrine (75 μg/kg/min. for 15 seconds, 7–8 μg/animal) was administered by means of a Braun perfusion apparatus. The dose of administered norepinephrine was established in preliminary tests so as to cause an arrythmia of a duration equal to or higher than 10 seconds. The arising time of the heart arrythmia starting from the beginning of the norepinephrine perfusion and the duration of the arrythmic phase were recorded. Tests of arrythmia duration for each animal were performed; thereafter the compounds of formula I and the compound R were administered intravenously or per os 2 minutes or 1 hour respectively before a fourth norepinephrine infusion. The activity of test compounds was evaluated as increasing percentage in the time of the arising of arrythmia as well as of the inhibition (duration of the arrythmic phase). For each dose at least 5 tests were performed. In table 9 we report as an example the $ED_{50}$ values defined as 50% reduction of the duration of arrythmias after the administration of both compound No. 8 and compound R either intravenously (i.v.) or per os (p.o.).

TABLE 9

Values of $ED_{50}$ (μg/kg) of compound No. 8 and of compound R in the test of norepinephrine-induced arrythmia.

| Compound | $ED_{50}$ i.v. (μg/kg) | $ED_{50}$ p.o. (μg/kg) |
|---|---|---|
| 8 | 125 | 350 |
| R | 650 | 4000 |

The data reported in table 9 confirm the values obtained in the test of reperfusion induced arrythmias in rat and show that compound No. 8, representative of the class of the compounds of formula I of the present invention, was much more active than the compound R when administered either intravenously or per os.

What we claim is:

1. A compound of formula (I)

wherein
R and $R_1$, equal to or different from each other, represent a hydrogen atom, a $C_1$-$C_3$ alkyl, a halogen atom, a $C_1$-$C_3$ alkoxy optionally substituted with a phenyl or a phenyl optionally substituted with from 1 to 3 substituents selected from $C_1$-$C_3$ alkyls, halogens, $C_1$-$C_3$ alkoxy groups;
Y represents an oxygen atom or a NH group;
$R_2$ represents a group selected from (A)

(B)

(C)

(D)

wherein
$R_3$ represents a $C_1$-$C_3$ alkyl;
n represents an integer selected from 2 and 3 and
m represents an integer selected from 1, 2 and 3; and salts thereof with pharmaceutically acceptable organic or inorganic acids.

2. A compound, according to claim 1, wherein $R_2$ represents a group selected from:
1-methyl-3-piperidinyl
1-ethyl-3-piperidinyl
1-methyl-4-piperidinyl
1-ethyl-4-piperidinyl
8-methyl-8-azabicyclo[3,2,1]oct-3-yl
9-methyl-9-azabicyclo[3,3,1]non-3-yl
8-methyl-8-azabicyclo[3,2,1]oct-2-yl
9-methyl-9-azabicyclo[3,3,1]non-2-yl
2-methyl-2-azabicyclo[2,2,1]hept-6-yl
2-methyl-2-azabicyclo[2,2,2]oct-6-yl
6-methyl-6-azabicyclo[3,2,2]non-9-yl
2-methyl-2-azabicyclo[2,2,1]hept-5-yl
2-methyl-2-azabicyclo[2,2,2]oct-5-yl
6-methyl-6-azabicyclo[3,2,2]non-8-yl
1-azabicyclo[2,2,1]hept-3-yl
1-azabicyclo[2,2,2]oct-3-yl
1-azabicyclo[3,2,2]non-6-yl.

3. A compound according to claim 1 wherein R and $R_1$, the same or different, are a hydrogen atom, a methyl group, a bromine or chlorine atom, a methoxy, a phenyl or a benzyloxy group; R₂ represents 1-methyl-3-piperidinyl, 1-ethyl-3-piperidinyl, 1-methyl-4-piperidinyl, 1-ethyl-4-piperidinyl, 8-methyl-8-azabicyclo[3,2,1]oct-3-yl, 8-methyl-8-azabicyclo[3,2,1]oct-2-yl, or 1-azabicyclo[2,2,2]oct-3-yl.

4. A pharmaceutical composition containing a therapeutically effective amount of a compound according to claim 1 in admixture with a pharmaceutically suitable carrier.

* * * * *